United States Patent
Srivastava et al.

(10) Patent No.: US 12,178,645 B2
(45) Date of Patent: Dec. 31, 2024

(54) ULTRASOUND DEVICE

(71) Applicant: BOSTON SCIENTIFIC SCIMED, INC., Maple Grove, MN (US)

(72) Inventors: Kyle Harish Srivastava, St. Paul, MN (US); Paul F. Chouinard, Maple Grove, MN (US); Christopher Piere, Hudson, WI (US); Jason A. Kilvington, Shoreview, MN (US); Niraj Prasad Rauniyar, Plymouth, MN (US); Brian P. Watschke, Minneapolis, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 261 days.

(21) Appl. No.: 16/913,947

(22) Filed: Jun. 26, 2020

(65) Prior Publication Data

US 2020/0405261 A1    Dec. 31, 2020

Related U.S. Application Data (60) Provisional application No. 62/868,644, filed on Jun. 28, 2019.

(51) Int. Cl.
  *A61B 8/00*  (2006.01)
  *A61B 1/307*  (2006.01)
  (Continued)

(52) U.S. Cl.
  CPC .............. *A61B 8/445* (2013.01); *A61B 8/08* (2013.01); *A61B 8/4461* (2013.01);
  (Continued)

(58) Field of Classification Search
  CPC ......... A61B 8/445; A61B 8/08; A61B 8/4461; A61B 8/4494; A61B 8/12; A61B 1/307;
  (Continued)

(56) References Cited

U.S. PATENT DOCUMENTS 9,687,166 B2 *  6/2017  Subramaniam ........ A61B 5/363
2003/0074039 A1 *  4/2003  Puskas .................. A61N 1/056
                                                   607/118

(Continued)

FOREIGN PATENT DOCUMENTS

EP    3449857 A1 *  3/2019  ......... A61B 18/1492
WO    0028901 A1    5/2000
         (Continued)

OTHER PUBLICATIONS

Satoh et al; "Intravesical Ultrasonography for Tumor Staging in an Orthotopically Implanted Rat Model of Bladder Cancer," The Journal of Urology, vol. 177, pp. 1169-1173, Mar. 2007.

(Continued)

*Primary Examiner* — John D Li
(74) *Attorney, Agent, or Firm* — Seager, Tufte & Wickhem, LLP (57) ABSTRACT

Example ultrasound medical devices are disclosed. An example medical device includes a support member having a proximal end region and a distal end region and a sensing member having a proximal end region and a distal end region, the distal end region of the sensing member coupled to the distal end region of the support member. The medical device also includes one or more ultrasound sensors disposed along the sensing member and a support shaft having a first end coupled to the sensing member and a second end coupled to the support member. Additionally, the sensing member is configured to shift from a first configuration in which the sensing member is adjacent to the support member to a second configuration in which at least a portion of the sensing member extends away from the support member.

19 Claims, 11 Drawing Sheets

(51) Int. Cl.
*A61B 8/08* (2006.01)
*A61B 8/12* (2006.01)
*A61M 25/00* (2006.01)

(52) U.S. Cl.
CPC ............ *A61B 8/4494* (2013.01); *A61B 1/307* (2013.01); *A61B 8/12* (2013.01); *A61B 8/4477* (2013.01); *A61M 25/0074* (2013.01)

(58) Field of Classification Search
CPC ........... A61B 8/4477; A61B 8/42–488; A61M 25/0074
See application file for complete search history.

(56) References Cited

U.S. PATENT DOCUMENTS

| | | | | |
|---|---|---|---|---|
| 2005/0215895 | A1* | 9/2005 | Popp | A61B 8/4494 600/437 |
| 2006/0241748 | A1* | 10/2006 | Lee | A61F 2/2445 623/2.37 |
| 2009/0171274 | A1* | 7/2009 | Harlev | A61B 5/6859 604/95.04 |
| 2010/0106149 | A1* | 4/2010 | Habib | A61B 18/082 606/28 |
| 2011/0166588 | A1* | 7/2011 | Connor | A61B 17/1214 606/191 |
| 2015/0366508 | A1* | 12/2015 | Chou | A61N 1/056 600/467 |
| 2016/0374710 | A1* | 12/2016 | Sinelnikov | A61B 17/3207 600/439 |
| 2018/0104455 | A1 | 4/2018 | Geva et al. | |
| 2019/0053821 | A1* | 2/2019 | Rem-Bronneberg | A61B 17/320068 |
| 2019/0110732 | A1* | 4/2019 | Toth | A61B 5/4875 |

FOREIGN PATENT DOCUMENTS

| | | |
|---|---|---|
| WO | 2005048813 A2 | 6/2005 |
| WO | 2014124231 A1 | 8/2014 |

OTHER PUBLICATIONS

International Search Report and Written Opinion dated Oct. 15, 2020 for International Application No. PCT/US2020/039952.

* cited by examiner

ULTRASOUND DEVICE

CROSS-REFERENCE TO RELATED APPLICATIONS

This application claims the benefit of priority of U.S. Provisional Application No. 62/868,644 filed Jun. 28, 2019, the entire disclosure of which is hereby incorporated by reference.

TECHNICAL FIELD

The present disclosure pertains to medical devices, and methods for manufacturing medical devices. More particularly, the present disclosure pertains to ultrasound visualization.

BACKGROUND

A wide variety of intracorporeal medical devices have been developed for medical use, for example, intravascular use. Some of these devices include ultrasound catheters, ultrasound devices, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example medical device includes a support member having a proximal end region and a distal end region and a sensing member having a proximal end region and a distal end region, the distal end region of the sensing member coupled to the distal end region of the support member. The medical device also includes one or more ultrasound sensors disposed along the sensing member and a support shaft having a first end coupled to the sensing member and a second end coupled to the support member. Additionally, the sensing member is configured to shift from a first configuration in which the sensing member is adjacent to the support member to a second configuration in which at least a portion of the sensing member extends away from the support member.

Alternatively or additionally, wherein the sensing member forms an arcuate shape in the second configuration.

Alternatively or additionally, wherein rotation of the support member rotates the sensing member around a longitudinal axis of the support member.

Alternatively or additionally, wherein each of the one or more ultrasound sensors are spaced away from one another along the sensing member.

Alternatively or additionally, wherein the distal end of the sensing member is fixedly attached to the distal end region of the support member.

Alternatively or additionally, wherein the second end of the support shaft is fixedly attached to the support member.

Alternatively or additionally, wherein the second end of the support shaft is translatable relative to the support member.

Alternatively or additionally, wherein the second end of the support shaft is coupled to the support member via an attachment collar, and wherein the attachment collar is designed to slide along the support member.

Alternatively or additionally, wherein the proximal end region of the sensing member is coupled to a hub, and wherein manipulation of the hub shifts the sensing member from the first configuration to the second configuration.

Alternatively or additionally, wherein rotation of a portion of the hub rotates the sensing member around a longitudinal axis of the support member.

Another example medical device for imaging the bladder includes a hub member coupled to an ultrasound sensing assembly. The ultrasound assembly includes a support member having a proximal end region and a distal end region and a sensing member having a proximal end region and a distal end region, the distal end region of the sensing member coupled to the distal end region of the support member. The ultrasound assembly also includes one or more ultrasound sensors disposed along the sensing member and a support shaft having a first end coupled to the sensing member and a second end coupled to the support member. Further, the sensing member is configured to shift from a first configuration in which the sensing member is adjacent to the support member to a second configuration in which at least a portion of the sensing member moves away from the support member.

Alternatively or additionally, wherein rotation of a portion of the hub member is designed to rotate the ultrasound assembly around a longitudinal axis of the support member.

Alternatively or additionally, wherein rotation of a portion of the hub member is designed to sweep the sensing member along an inner surface of the bladder when the sensing member is in the second configuration.

Alternatively or additionally, wherein the sensing member forms an arcuate shape in the second configuration.

Alternatively or additionally, wherein each of the one or more ultrasound sensors are spaced away from one another along the sensing member.

Alternatively or additionally, wherein the distal end of the sensing member is fixedly attached to the distal end region of the support member.

Alternatively or additionally, wherein the second end of the support shaft is fixedly attached to the support member.

Alternatively or additionally, wherein the second end of the support shaft is translatable relative to the support member.

An example method for imaging the bladder includes positioning an ultrasound catheter assembly into the bladder. The ultrasound catheter assembly includes a support member having a proximal end region and a distal end region and a sensing member having a proximal end region and a distal end region, the distal end region of the sensing member coupled to the distal end region of the support member. The ultrasound catheter assembly also includes one or more ultrasound sensors disposed along the sensing member and a support shaft having a first end coupled to the sensing member and a second end coupled to the support member. The method also includes translating the sensing member relative to the support member such that at least a portion of the sensing member moves away from the support member.

Alternatively or additionally, the method further comprising rotating the sensing member around a longitudinal axis of the support member, such that the sensing member sweeps around an inner surface of the bladder.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Ultrasound imaging is a medical procedure that may be used to detect and characterize abnormal tissue growth that occurs with a variety of medical conditions. In use, ultrasound medical devices may project sound waves that bounce against organs and reverberate back to a transducer, whereby the transducer processes the reflected waves and converts them into an image of targeted organs or tissues. In some instances, an ultrasound device may be used to mark out the boundaries of a cancer tumor prior to its removal. For example, a physician may utilize ultrasound to visualize and characterize bladder cancer tumors.

A fundamental aspect to treating bladder cancer is establishing proper visualization of the interior of the bladder. Specifically, in some instances it may be desirable to position an ultrasound detection device near the cancer tumors prior to imaging. Imaging cancers tumors in close proximity may provide several advantages over less invasive imaging. Namely, imaging in close proximity may allow the detection of smaller tumors in addition to being able to more accurately assess the depth of a specific tumor.

Therefore, in some instances, it may be desirable to utilize an ultrasound imaging device to image the inner surface of a bladder while in close proximity to the inner surface of a bladder. Some of the medical devices disclosed herein may include utilizing a flexible and expandable ultrasound device, whereby the ultrasound device may be designed to permit a physician to image the interior surface of a bladder while in close proximity to the surface.

Figure 1:
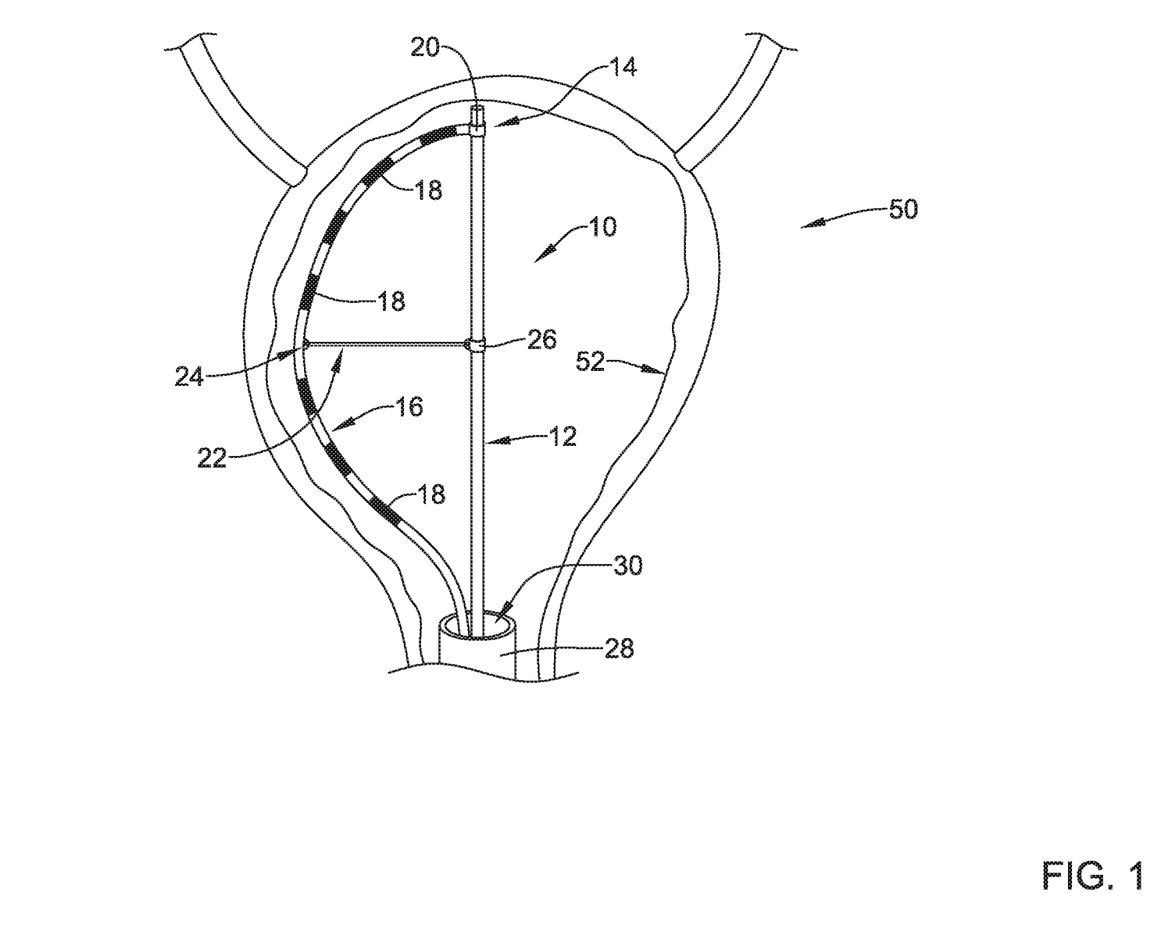
FIG. 1 is a plan view of an example medical device positioned within a bladder.

FIG. 1 is a schematic view of an ultrasound medical device 10 which may be utilized to access and treat a tissue region in the body. Specifically, FIG. 1 generally shows the medical device 10 deployed within the inner cavity of a bladder 50. However, this is not intended to be limiting. Rather, it can be appreciated the ultrasound medical device 10 may be utilized in other regions of the body. For example, while the illustrated embodiment shows the device 10 being used for treating the bladder, the device 10 (and the methods described herein) may alternatively be configured for use in other tissue applications, such as procedures for treating tissue in the kidney, abdominal organs, upper and lower urinary tract, vagina, uterus, stomach, etc.

As illustrated in FIG. 1, in some instances the ultrasound medical device 10 may be delivered to a tissue site (e.g., to a cancer site along an inner surface of the bladder 50) via one or more catheters. For example, FIG. 1 illustrates that the ultrasound device 10 may be advanced through the lumen 30 of a catheter 28. It is contemplated that the catheter 28 may be utilized to both deliver and/or retrieve the ultrasound device 10. For example, the ultrasound device 10 may be advanced through the lumen 30 of the catheter 28 in a collapsed configuration. Further, the ultrasound device 10 may be advanced out the distal end of the catheter 28, whereby at least a portion of the ultrasound device 10 may shift from a first (e.g., collapsed, pre-deployment, etc.) configuration to a second (e.g., expanded, deployed, etc.) configuration. It is further contemplated that the catheter 28 may include a guide catheter, delivery catheter, endoscope, cystoscope, etc.

As discussed above, it can be appreciated that the catheter 28 may be utilized to retrieve the ultrasound device 10 after a medical procedure is completed. For example, after completion of an ultrasound imaging procedure, a physician may retract the ultrasound device 10 in a proximally into the distal end of the catheter 28. While not illustrated in FIG. 1, it is contemplated that the catheter 28 may include a tapered distal end. It can be appreciated that a tapered end of the catheter 28 may be designed to funnel the ultrasound device 10 into the lumen 30 of the catheter 28.

While FIG. 1 illustrates the catheter 28 including a single lumen 30, it is contemplated that, in some examples, the catheter 28 may include two or more lumens designed to permit the ultrasound device 10 to be advanced therethrough. For example, in some instances the catheter 28 may be an endoscope, cystoscope, etc. which may include a first lumen to permit fluid to be passed therethrough (and into the bladder) and a second lumen (e.g., a working channel) designed to permit the ultrasound device 10 to be advanced therethrough FIG. 1 further illustrates that the ultrasound device 10 may include a support shaft 12 (e.g., catheter, tubular member, etc.) having a proximal end portion and a distal end portion 14. FIG. 1 illustrates the support shaft 12 extending through the lumen 30 of the catheter 28. In some instances, the support shaft 12 may be a solid member. However, in other examples, the support shaft 12 may be defined as a tubular member including a lumen extending therein. In other words, the support shaft 12 may include a lumen which extends along the entire length of the support shaft 12 or the lumen may extend along only a portion of the support shaft 12. The lumen of the support shaft 12 may be sized and/or shaped to accommodate a guidewire to extend therein.

FIG. 1 further illustrates that the ultrasound device 10 may include a sensing member 16. The sensing member 16 may include a distal end region 20 and a proximal end region. As illustrated in FIG. 1, the distal end region 20 may be coupled to the distal end region 14 of the support shaft 12. In some examples, the distal end region 20 of the sensing member 16 may be rigidly attached to the distal end region 14 of the support shaft 12. In other examples, however, the distal end region 20 of the sensing member 16 may move with respect to the distal end region 14 of the support shaft 12. For example, the distal end region 20 of the sensing member 16 may be coupled to the distal end region 14 of the support shaft via a swivel, collar, or the like.

As illustrated in FIG. 1, in some instances, the sensing member 16 may include one or more ultrasound sensors 18 disposed along the sensing member 16. The ultrasound sensors 18 may be spaced apart from one another along the length of the sensing member 16. Further, in some examples, each of the ultrasound sensors 18 may be relatively flat, whereby the outer surface of the sensor is designed to be positioned against (or adjacent) a target tissue site (e.g., cancerous tumor). In other examples, however, the ultrasound sensors 18 may be include a variety of shapes and/or configurations. For example, the sensors 18 may be embedded within the body of the sensing member 16 or may wrap around the body of the sensing member 16. In some examples, the ultrasound sensors 18 may include phased array transducers and/or rotational (e.g., spinning) transducers. Further, in other examples the transducers (e.g., phased array, rotational, etc.) may be selected according to the resolution and penetration depth required during an ultrasound procedure.

FIG. 1 further illustrates that the ultrasound device 10 may include a support member 22 (e.g., support arm, tether, etc.). The support member 22 may include a first end 24 and a second end 26. As shown in FIG. 1, the first end 24 of the support member 22 may be coupled to the sensing member 16 and the second end 26 of the support member 22 may be coupled to the support shaft 12.

As will be discussed in greater detail below, in some instances it may be desirable for the support member 22 to translate relative to the support shaft 12. Therefore, it can be appreciated that, in some examples, the second end 26 of the support member 22 may include a collar slidably coupled to the support shaft 12. In other words, in some examples, the second end 26 of the support member 22 may wrap around the outer surface of the support shaft 12, thereby permitting the second end 26 of the support member 22 to slide proximally and distally along the support shaft 12 (e.g., along the longitudinal axis of the support shaft 12).

Figure 2:
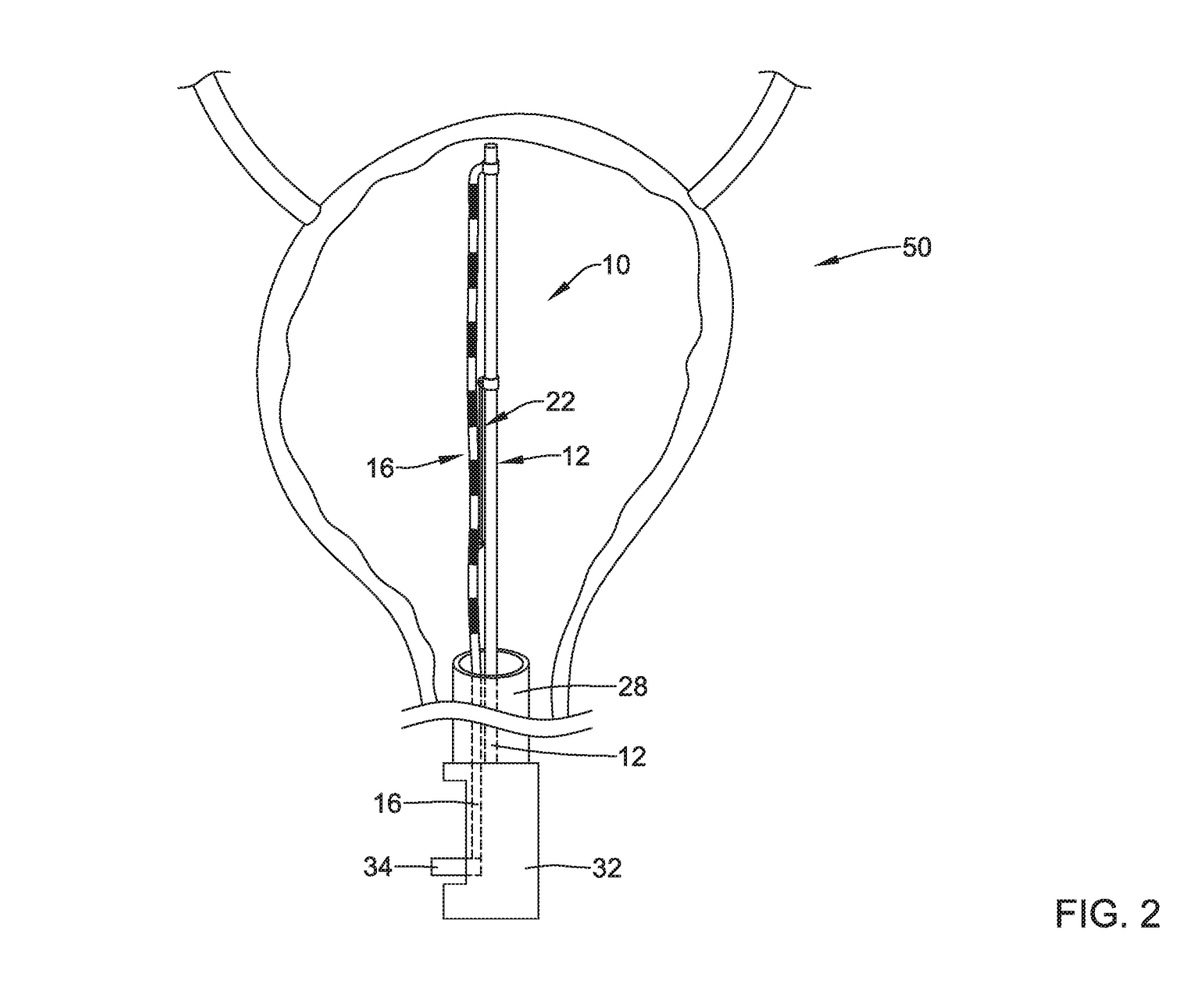
FIGS. 2-4 illustrate a series of steps showing an example medical being advanced within an example delivery catheter and deployed within a bladder.
Figure 3:
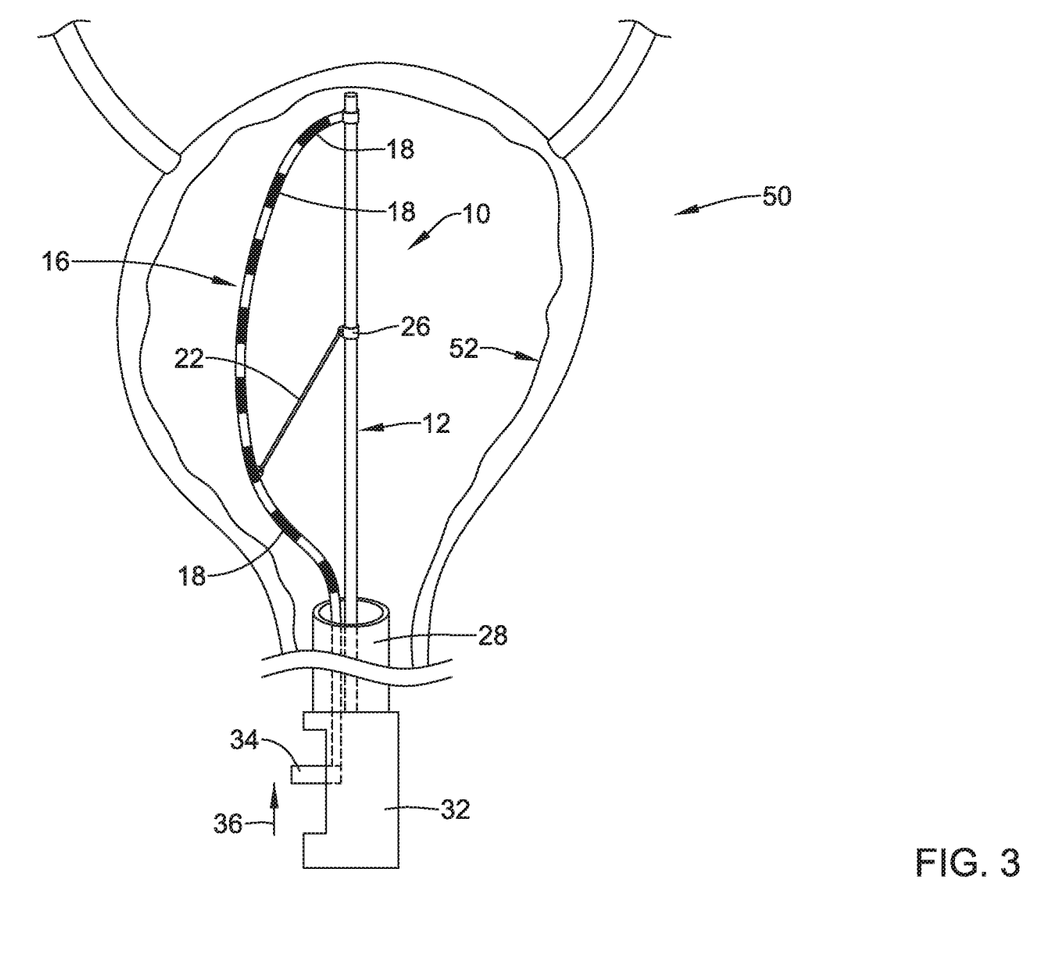
Figure 4:
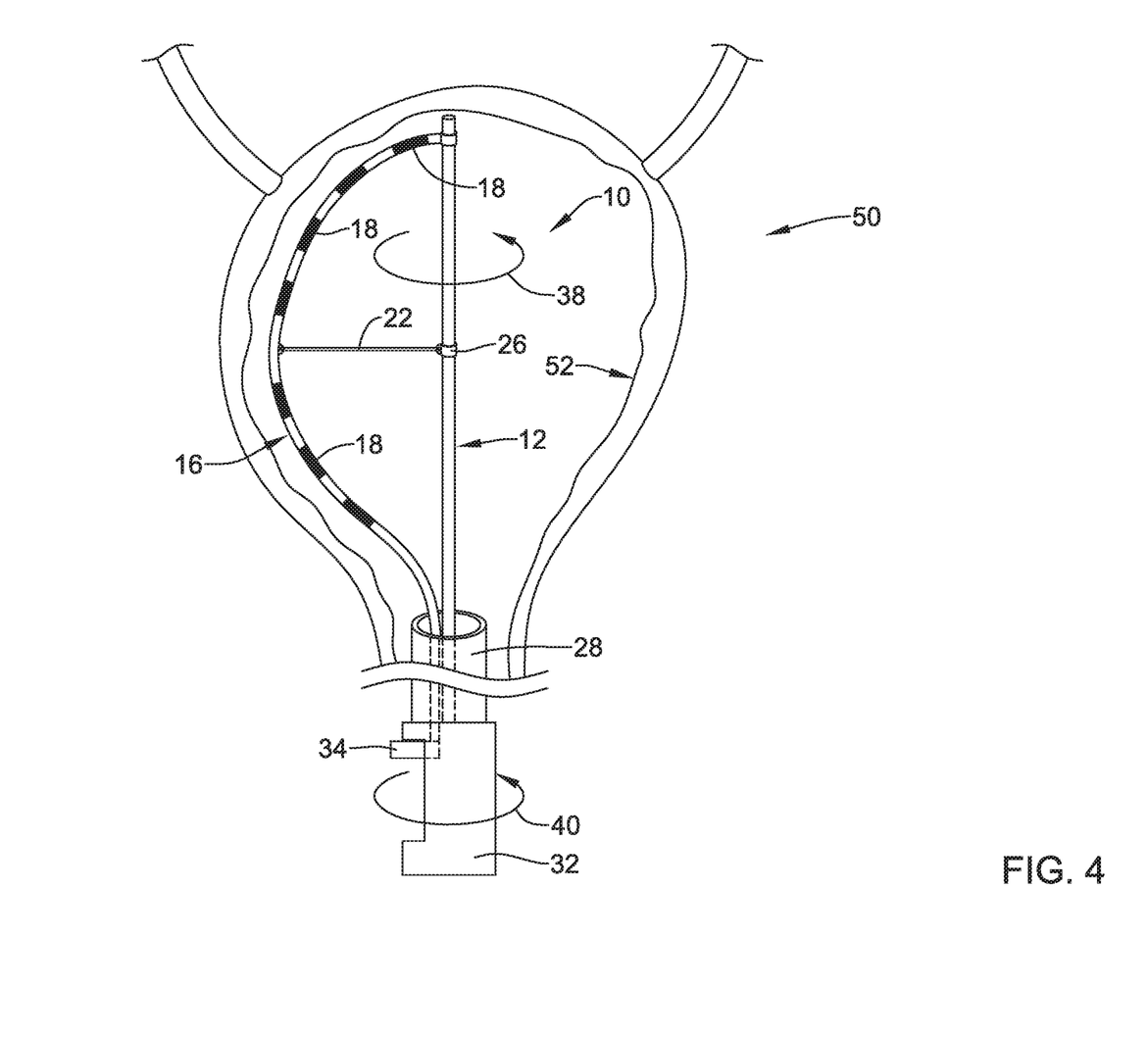

FIGS. 2-4 illustrate example steps to position, deploy and manipulate the ultrasound device 10 in a bladder. For example, FIG. 2 illustrates the ultrasound device 10 (including the support shaft 12, the sensing member 16 and the support member 22) extending through the lumen 30 of the catheter 28. Further, FIG. 2 illustrates that, in some examples, the proximal end of the catheter 28 may be coupled to a hub member 32. The hub member 32 may include an actuator 34. It can be appreciated that the actuator 34 may translate in a channel of the hub member 32. For example, it can be appreciated that the actuator 34 may be able to translate in a proximal and/or distal direction within the channel of the hub member 32.

Additionally, FIG. 2 illustrates that, in some examples, the proximal end of the sensing member 16 may be coupled to the actuator 34. Further, FIG. 2 illustrates that the proximal end of the support shaft 12 may be rigidly fixed to a portion of the hub member 32. In some examples, the hub member 32 may include a lumen and/or passage extending therethrough which substantially aligns with a lumen of the support shaft 12 (for examples in which the support shaft 12 includes a lumen). Like that described with respect to the support shaft 12, it can be appreciated that the lumen of the hub member 32 may be sized and/or shaped to accommodate a guidewire extending therethrough. It can be further appreciated that the hub member 32 may include one or more features which manipulate a least a portion of the ultrasound device 10 within a body cavity (e.g., in a bladder). For example, it can be appreciated that via manipulation of the actuator 34, the sensing member 16 may be able to translate relative to the support shaft 12.

For example, FIG. 2 illustrates the actuator 34 after having been retracted in a proximal direction within the channel in the hub member 32. It can be appreciated that the proximal retraction of the actuator 34 may draw the sensing member 16 in a proximal direction such that the sensing member 16 is substantially adjacent (e.g., aligned, parallel) to the support shaft 12. Further, proximal retraction of the actuator 34 may also result in the rotation (e.g., pivoting, sliding, translation) of the support shaft 12 such that the support member 22 is substantially adjacent (e.g., aligned, parallel) to the support shaft 12 and/or the sensing member 16.

FIG. 3 illustrates the ultrasound device 10 after the actuator 34 has been advanced in a distal direction (as shown by arrow 36) within the channel of the hub member 32. FIG. 3 further illustrates that the distal translation of the actuator 34 may result in the sensing member 16 to begin to bow away from the support shaft 12. FIG. 3 illustrates that during this process the sensing member 16 begins to form a slight curve. In other words, as the actuator 34 is translated distally, at least a portion of the sensing member may move radially away from the support shaft 12 (e.g., curving away from the support shaft 12), thereby shifting the ultrasound sensors 18 to a position closer to the inner surface 52 of the bladder 50. Additionally, FIG. 3 illustrates that coincident with the movement of the sensing member 16, the support member 22 may move (e.g., pivot, rotate, slide) with respect to the sensing member 16 and/or the support shaft 12.

FIG. 4 illustrates the ultrasound device 10 after the actuator 34 has been further advanced in a distal direction within the channel of the hub member 32. FIG. 4 further illustrates that the distal translation of the actuator 34 may result in the sensing member 16 bowing away from the support shaft 12 to a greater extent as compared to its position in FIG. 3. For example, FIG. 4 illustrate the sensing member 16 having a greater curve as compared to its position as illustrated in FIG. 3. Accordingly, it can be appreciated that translating the sensing member 16 in a proximal-to-distal direction relative to the support shaft 12 may result in the ultrasound sensors 18 being shifted to a position closer to the inner surface 52 of the bladder 50. Additionally, FIG. 4 illustrates that translating the sensing member 16 in a proximal-to-distal direction relative to the support shaft 12 results in the support member 22 moving (e.g., pivoting, rotating, sliding) with respect to the sensing member 16 and/or the support shaft 12.

FIG. 4 further illustrates, that in some examples, rotation of at least a portion of the hub member 32 may rotate one or more features of the ultrasound device 10 within a body cavity (e.g., within the bladder). For example, FIG. 4 illustrates that rotation of the hub member 32 (as shown by the around 40) may rotate the sensing member 16, the support member 22 and/or the support shaft 12 around the longitudinal axis of the support shaft 12. Rotation of one or more components of the ultrasound device 10 within the bladder 50 is shown by the arrow 38 in FIG. 4.

While the above discussion illustrates that rotation of the hub member 32 may rotate the ultrasound device 10 (including the support shaft 12, the support member 22, the sensing member 16 and/or the catheter 28) the within a body cavity (e.g., the bladder), it is not intended to be limiting. Rather, it is contemplated that the ultrasound device 10 may include alternative features and/or designs which permit the translation of the sensing member 16 with respect to the support shaft 12 and/or the rotation of the ultrasound device 10 (and components thereof) within the body cavity. For example, in some instances the ultrasound device may include a screwdrive, rack and pinon, or other features which permit the translation of the sensing member 16 with respect to the support shaft 12 and/or the rotation of the ultrasound device 10 (and components thereof) within the body cavity.

Figure 5:
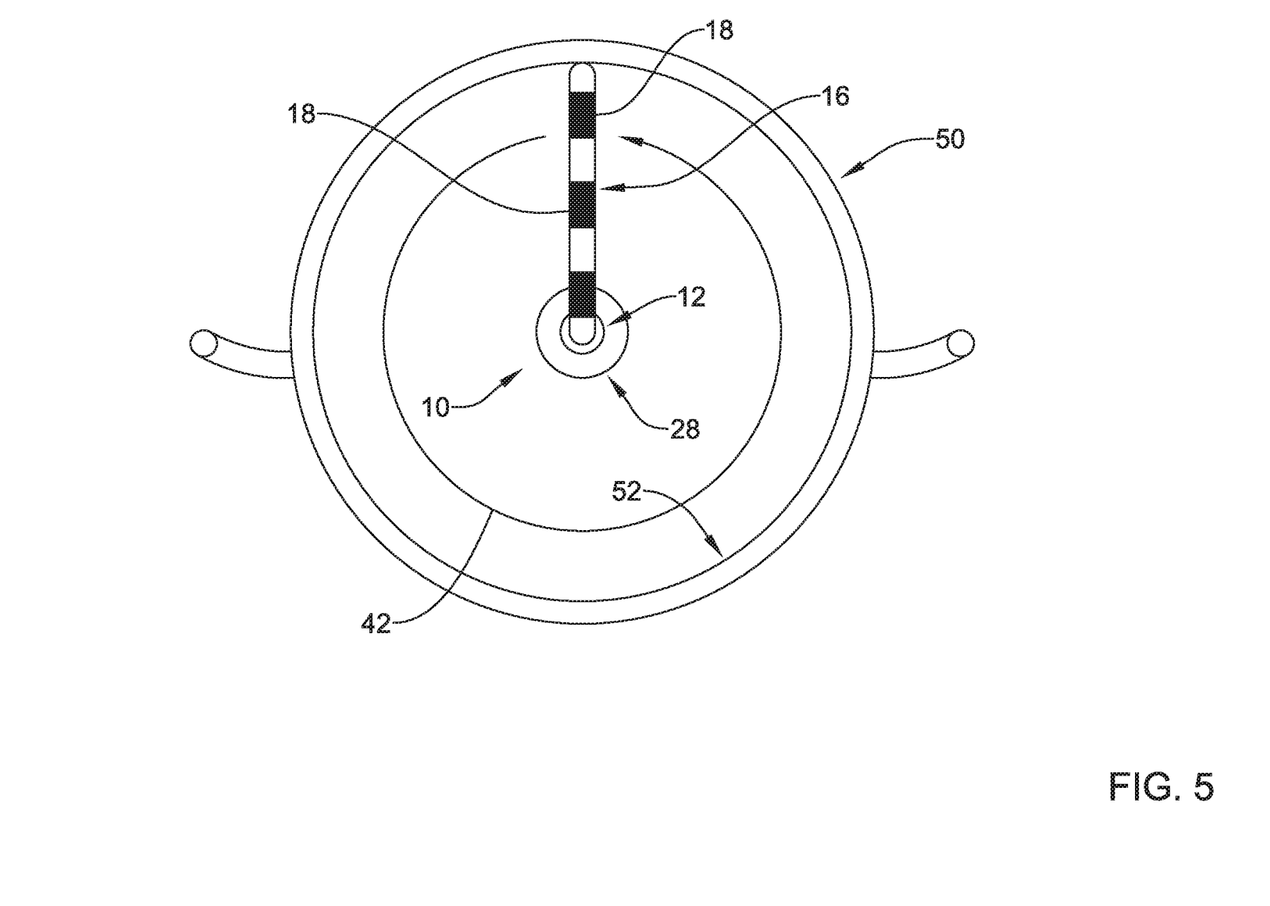
FIG. 5 illustrates a partial cross-sectional view of the example medical device being manipulated within a bladder.

FIG. 5 illustrates a top-view of the ultrasound device 10 shown in FIG. 4 positioned within the bladder 50. For example, FIG. 5 illustrates the support shaft 12 positioned with the lumen of the catheter 28. Additionally, FIG. 5 illustrates the sensing member 16 extending away from the support shaft 12 such that the ultrasound sensors 18 are positioned adjacent to the inner surface 52 of the bladder 50. Further, FIG. 5 illustrates that the rotation of the sensing member 16 (as shown by the arrow 42) may "sweep" the sensing member 16 (including the ultrasound sensors 18) along the inner surface 52 of the body cavity (e.g., the bladder 50). It can be appreciated that is may be possible to rotate the sensing member through any angle of rotation (0-360 degrees) around the longitudinal axis of the support member 12. Further, it is contemplated that the sensing member 16 may be rotated more than 360 degrees around the longitudinal axis of the support member 12.

It can be appreciated from the above discussion (and illustrations shown in FIGS. 1-4) that 360-degree rotation of the sensing member 16 may permit complete imaging of the inner surface of a body cavity (e.g., the bladder 50). In other words, because the ultrasound sensors 18 may extend from the distal end region of the sensing member 16 to adjacent the opening of the catheter 28, the sensing member 16 may image the inner cavity of the bladder from top to bottom as the sensing member 16 is rotated (e.g., swept) through a full 360-degree angle. Further, in some examples, the images acquired from one or more of the sensors 18 may be able to be stitched together to create a 360-degree rendering of the bladder, including the specific "depth" of cancerous tumors extending into the bladder wall. However, this is not intended to be limiting. Rather, it is contemplated that, in some instances, the sensing member 16 (including the ultrasound sensors 18) may be designed such that individual sensors 18 may be activated independent of other sensors 18. Therefore, it is contemplated that, in some examples, a physician may be able to customize an ultrasound imaging pattern via selective activation of sensors 18.

Figure 6:
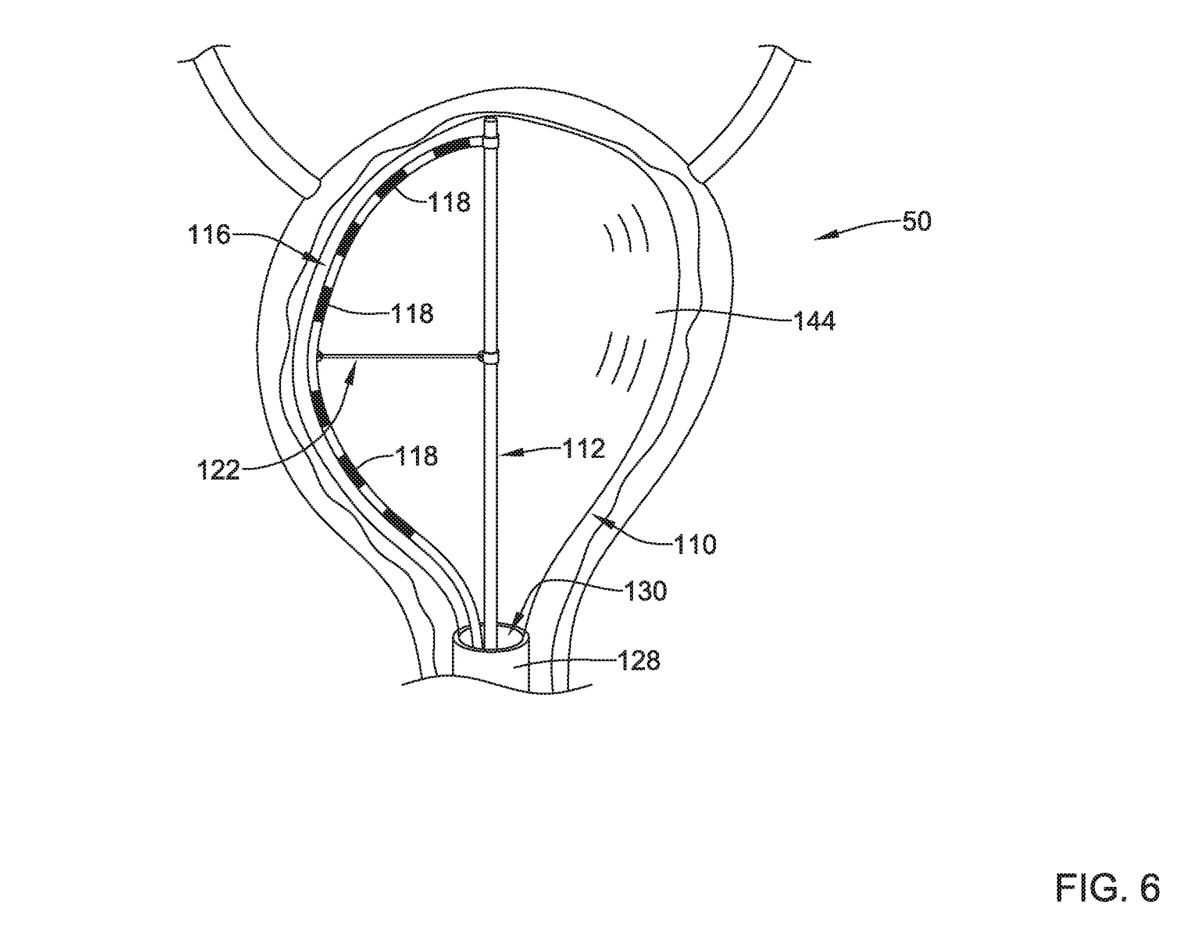
FIG. 6 is a plan view of another example medical device positioned within a bladder.

FIG. 6 illustrates another example medical device 110. Medical device 110 may be similar in form and function as the medical device 10 described above. For example, the medical device 110 may include a sensing member 116 (including ultrasound sensors 118 disposed thereon) and a support member 122 coupled to a support shaft 112. However, FIG. 6 further illustrates that the sensing member 116, the support member 122 and/or the support shaft 112 may be positioned within an expandable balloon member 144. Further, FIG. 6 illustrates that the medical device 110 (including the sensing member 116, the support member 122, the support shaft 112 and the balloon 144) may be advanced through the lumen 130 of a delivery catheter 128.

Additionally, it can be appreciated that, in some examples, the expandable balloon member 144 may be inflated with a fluid. Further, it is contemplated that the ultrasound device 110 may be rotated (as described above) while positioned in the expandable balloon member 144. Accordingly, the ultrasound transducers 118 may be immersed in fluid as they are rotated within the fluid-filled expandable balloon member 144. It can be appreciated that collecting ultrasound images of tissue utilizing sensors 118 which are immersed in fluid may be desirable because the fluid may improve the resolution of the ultrasound images.

Figure 7:
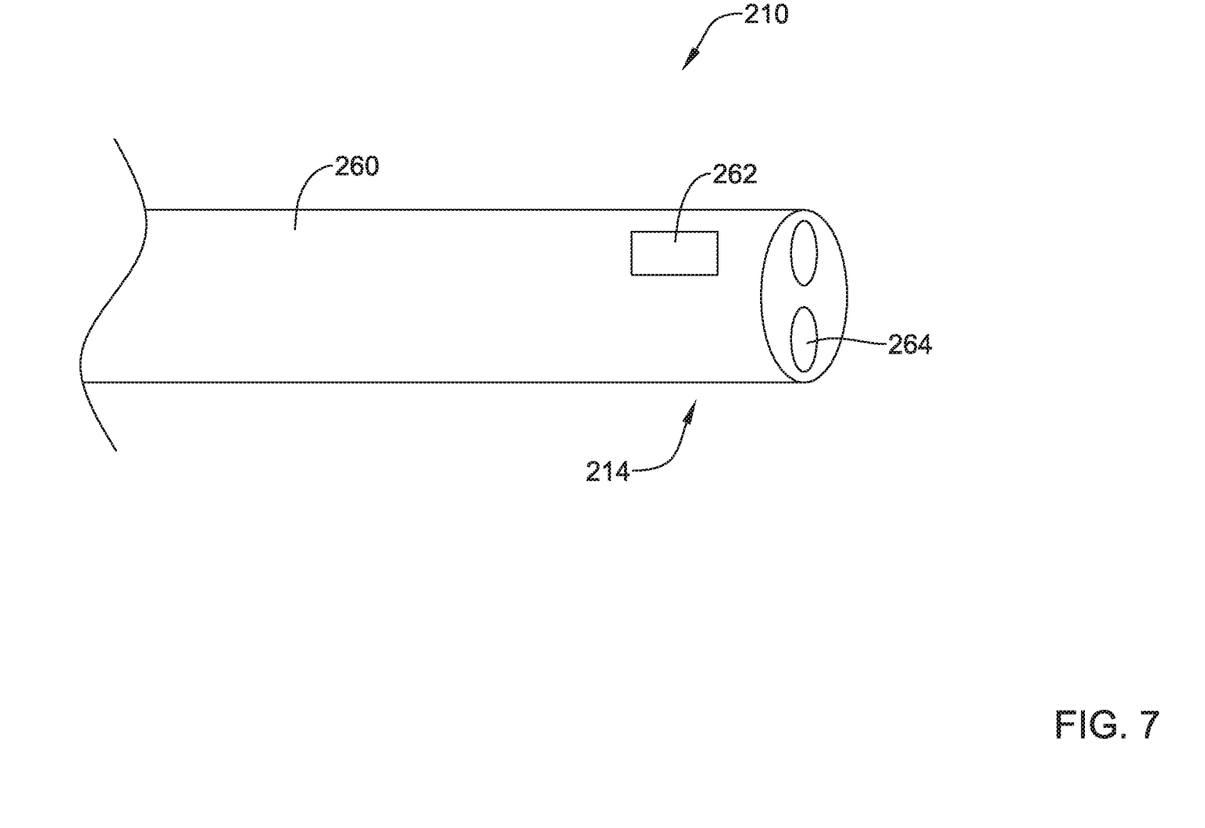
FIG. 7 illustrates another example medical device.

FIG. 7 illustrates another example medical device 210. Medical device 210 may include an ultrasound catheter. The ultrasound catheter 210 may include a shaft 260 having a distal end region 214 and a proximal end region. The distal end region 214 of the medical device 210 may include an ultrasound transducer 262 disposed along its outer surface. Furthermore, the medical device 210 may include a camera 264 disposed along a forward-facing portion of the medical device 210. It can be appreciated that, in some examples, the forward-facing camera 264 may provide real-time visualization of the portion of the tissue (e.g., inner surface of a bladder) for which ultrasound imaging is being collected (via the ultrasound transducer 226). Providing real-time visualization (via the camera 264) of ultrasound imaging may be desirable because clinicians are often accustomed to direct visualization. Further, coupling ultrasound with real-time camera visualization may allow a clinician to utilize ultrasound to confirm that all tissue was removed/collected after a resection procedure was performed using the real-time camera visualization. Similarly, ultrasound may be utilized to confirm or prevent perforation of a tissue target site during a resection or tumor removal.

Figure 8:
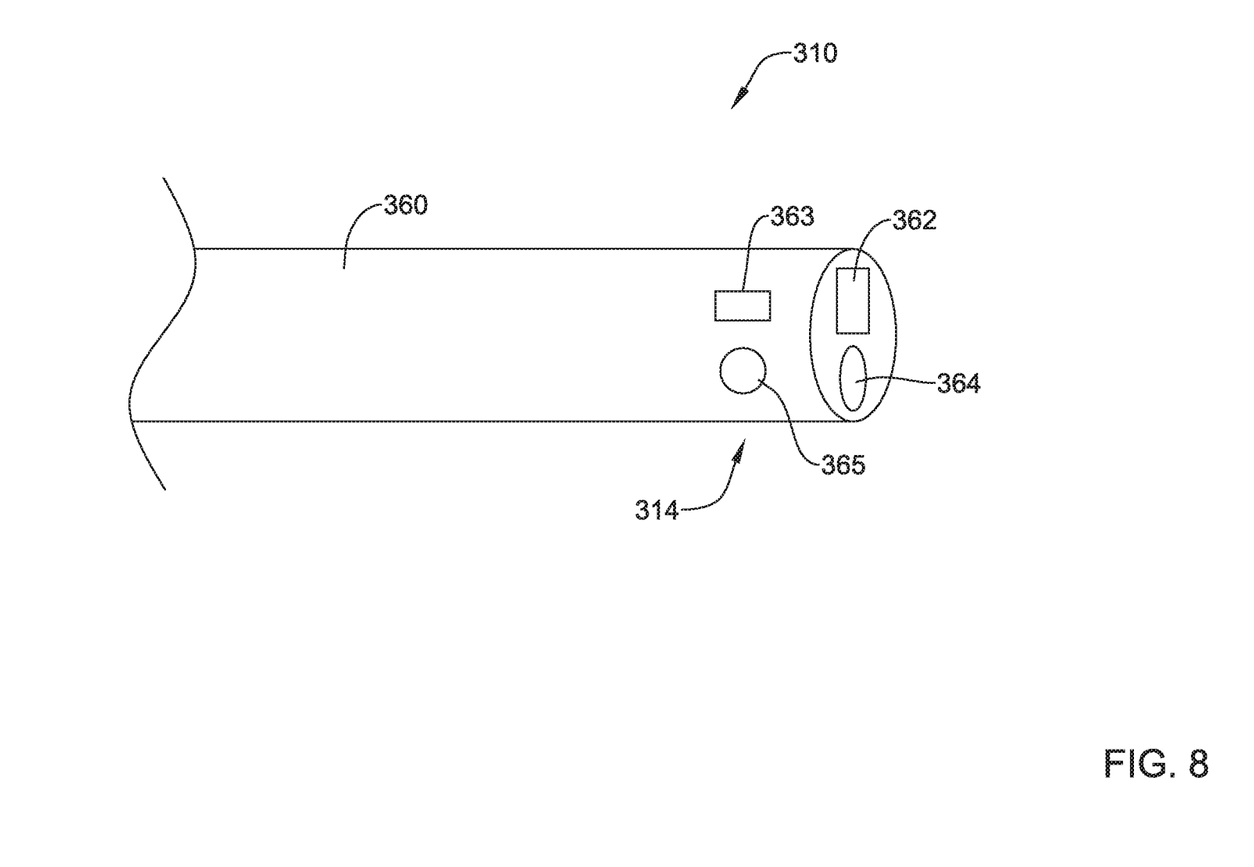
FIG. 8 illustrates another example medical device.

FIG. 8 illustrates another example medical device 310. Medical device 310 may include an ultrasound catheter. The ultrasound catheter 310 may include a shaft 360 having a distal end region 314 and a proximal end region. The distal end region of the medical device 310 may include an ultrasound transducer 362 disposed along a forward-facing portion of the medical device 310. Furthermore, the medical device 310 may also include a camera 364 disposed along a forward-facing portion of the medical device 310. It can be appreciated that, in some examples, the forward-facing camera 364 may provide real-time visualization of the portion of the tissue target site (e.g., inner surface of a bladder) for which ultrasound imaging is be collected (via the ultrasound transducer 326).

FIG. 8 further illustrates that, in some examples, the ultrasound catheter 310 may include a second ultrasound transducer 363 positioned on a side portion of the ultrasound catheter 310. Additionally, FIG. 8 illustrates that the ultrasound catheter 310 may include a second camera 365 positioned on a side portion of the ultrasound catheter 310. It can be appreciated that, in some examples, having two cameras collecting information from two different orientations (e.g., forward-facing and side-facing) may improve visualization of the body cavity in which the ultrasound catheter 310 is positioned. Further, it can be appreciated that both the forward-facing camera 364 and the side-facing camera 365 may work collaboratively with the forward-facing ultrasound transducer 362 and the side-facing transducer 363 to confirm that the ultrasound was appropriately deployed to image the entire cavity and/or provide feedback as to areas of the target tissue that were missed during a preliminary ultrasound sweep of the body cavity. In other words, having the camera imaging (e.g., forward-facing, side-facing or both) may correlate with real time ultrasound imaging to help guide resection and/or treatment of tissue sites (e.g., target cancerous tumors).

Figure 9:
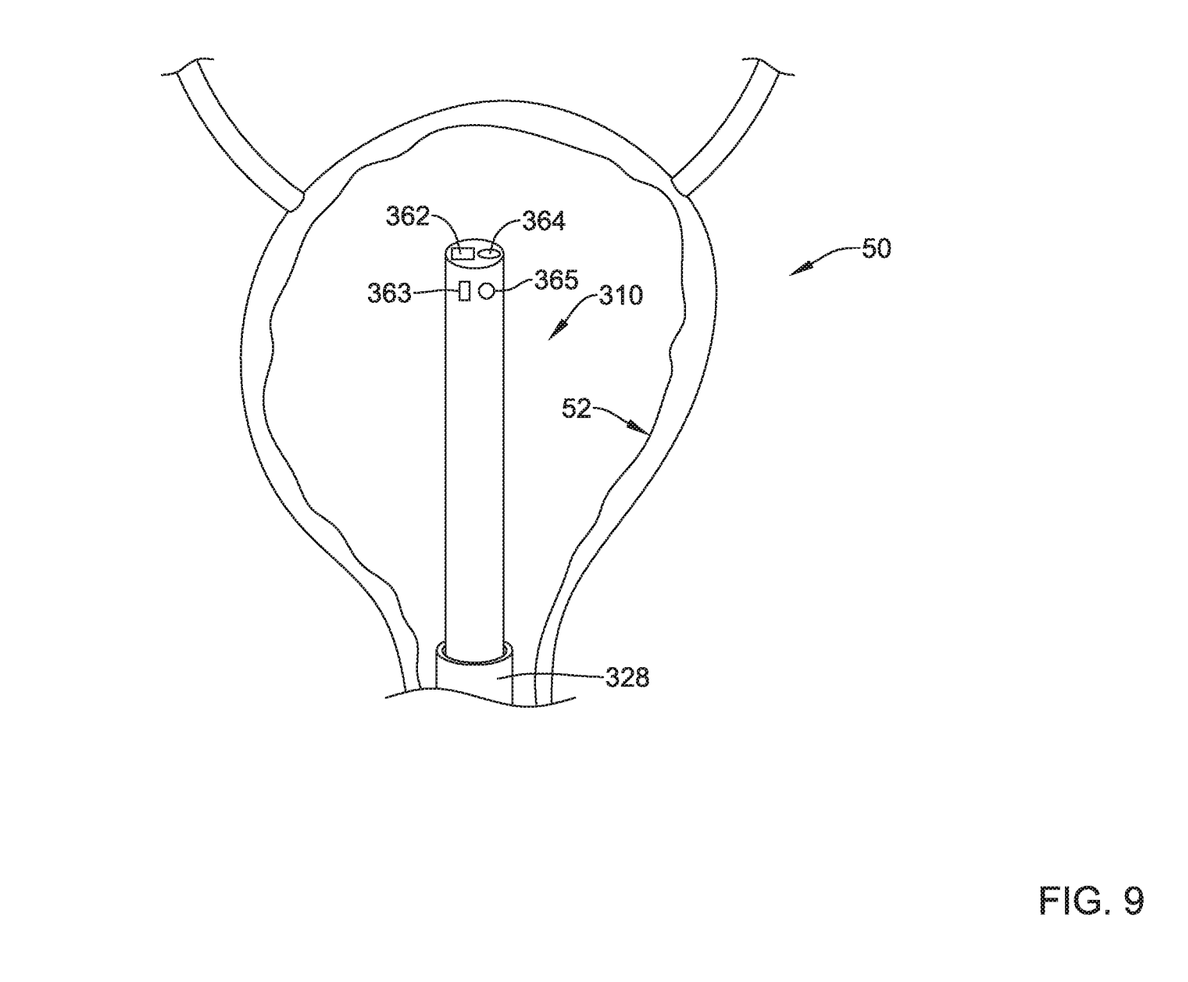
FIG. 9 illustrates the example medical device shown in FIG. 8 positioned within a bladder.

FIG. 9 illustrates the example medical device (e.g., ultrasound catheter) 310 positioned in a bladder 50. FIG. 9 illustrates that the ultrasound catheter 310 may be advanced through a lumen of a delivery catheter 328 to a position within a body cavity (e.g., within a bladder). Additionally, FIG. 9 illustrates that the ultrasound catheter 310 may be advanced such that the ultrasound transducer 362 and the camera 364 are forward-facing and directed toward the inner surface 52 of the bladder while the ultrasound transducer 363 and the camera 365 are side-facing and directed toward the inner surface 52 of the bladder. It can be appreciated that a physician may be able to control the proximity in which both ultrasound transducers 362/363 and both cameras 364/365 are from the inner surface 52 of the bladder 50 via manipulation of the proximal end of the ultrasound catheter 310. It can be further appreciated that the physician may be able to simultaneously receive both real-time ultrasound imaging and video visualization of a tissue target site via the forward-facing ultrasound transducer 362 and camera 364 and the side-facing ultrasound transducer 363 and camera 365.

Figure 10:
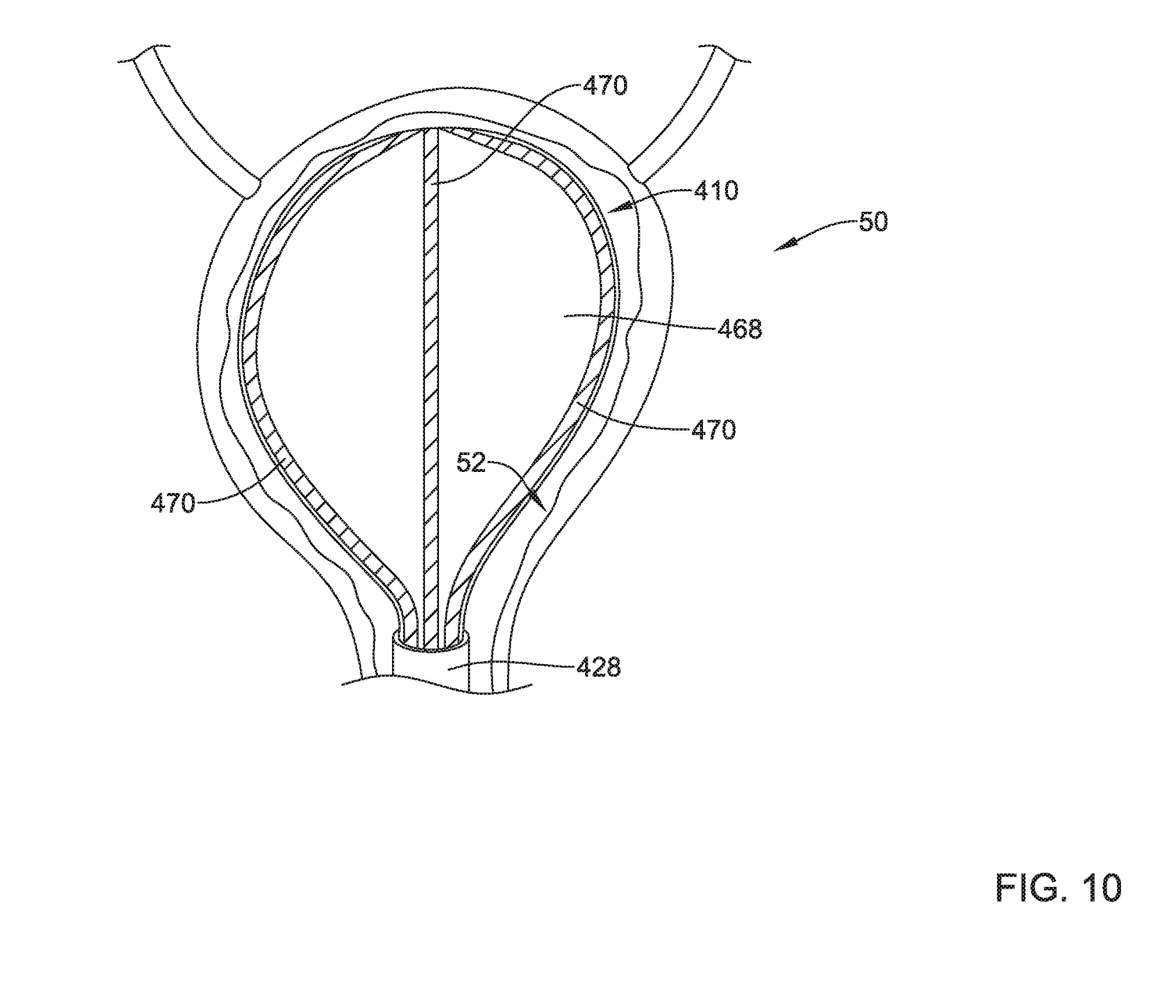
FIG. 10 illustrates another example medical device.

FIG. 10 illustrates another example medical device 410. The medical device 410 may include an expandable balloon member 468. The expandable balloon member 468 may be advanced through a delivery catheter 428 and expanded within a body cavity (e.g., within the bladder 50). Therefore, it can be appreciated that, once expanded, the balloon 468 may contact the inner surface 52 of the bladder 50.

Additionally, FIG. 10 illustrates that, in some examples, the medical device 410 may include one or more lumens 470 (e.g., channels, passages, etc.) extending within the wall of the expandable balloon member 468. These lumens 470 may extend vertically from a distal end region of the balloon 468 to the proximal end region of the balloon 468. Further, the medical device 410 may include one or more features which permit an ultrasound catheter (e.g., an ultrasound catheter including an ultrasound sensor) to be positioned within and translate within) the lumens 470. It can be appreciated that positioning an ultrasound transducer within one or more of the lumens 470 may permit the ultrasound transducer to acquire ultrasound images while in close proximity to a target tissue site (e.g., cancerous tumor).

Figure 11:
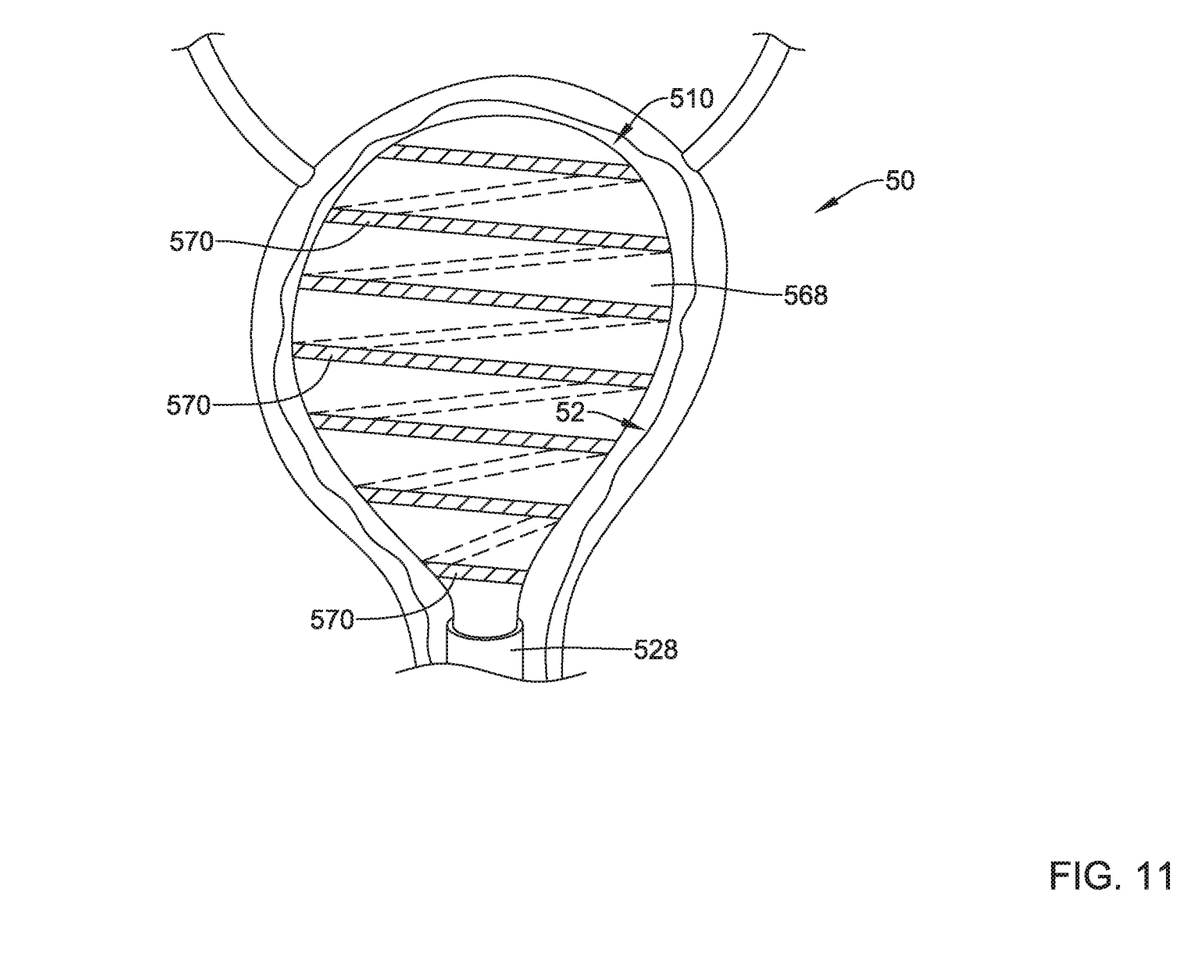
FIG. 11 illustrates another example medical device.

FIG. 11 illustrates another example medical device 510. The medical device 510 may include an expandable balloon member 568. The expandable balloon member 568 may be advanced through a delivery catheter 528 and expanded within a body cavity (e.g., within the bladder 50). Therefore, it can be appreciated that, once expanded, the balloon 568 may contact the inner surface 52 of the bladder 50.

Additionally, FIG. 11 illustrates that, in some examples, the medical device 510 may include a lumen 570 (e.g., channels, passages, etc.) extending within the wall of the expandable balloon member 568. The lumen 570 may extend helically around the balloon member 568 from a distal end region of the balloon 568 to the proximal end region of the balloon 568. Further, the medical device 510 may include one or more features which permit an ultrasound catheter (e.g., an ultrasound catheter including an ultrasound sensor) to be positioned within and translate within) the lumen 570. It can be appreciated that positioning an ultrasound transducer within the lumen 570 may permit the ultrasound transducer to acquire ultrasound images while in close proximity to a target tissue site (e.g., cancerous tumor).

Some example materials that can be used for the various components of the medical device 10 (or other components of medical device 10) and other medical devices disclosed are described herein. However, this is not intended to limit the devices and methods described herein. Rather, it is contemplated that a variety of materials may be used for the various components of the medical device 10 and other medical devices described herein.

The medical device 10 (or other components of medical device 10) and other medical devices disclosed herein may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex® high-density polyethylene, Marlex® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon®), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of the medical device 10 (or other components of medical device 10) and other medical devices disclosed herein may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the medical device 10 (or other components of medical device 10) and other medical devices disclosed herein in determining its location. Some examples of radiopaque materials may include, but are not limited to, gold, platinum, palladium, tantalum, tungsten alloy, polymer material loaded with radiopaque filler, and the like. Additionally, other radiopaque marker bands and/or coils may also be incorporated into the design of the medical device 10 (or other components of medical device 10) and other medical devices disclosed herein to achieve the same result.

In some embodiments, a degree of Magnetic Resonance Imaging (MM) compatibility is imparted into the medical device 10 (or other components of medical device 10) and other medical devices disclosed herein. For example, the medical device 10 (or other components of medical device 10) and other medical devices disclosed herein, or portions thereof, may be made of a material that does not substantially distort the image and create substantial artifacts (e.g., gaps in the image). Certain ferromagnetic materials, for example, may not be suitable because they may create artifacts in an MM image. The medical device 10 (or other components of medical device 10) and other medical devices disclosed herein, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A medical device, comprising:
   a support shaft having a proximal end region and a distal end region;
   a sensing member having a proximal end region and a distal end region, the distal end region of the sensing member coupled to the distal end region of the support shaft;
   one or more ultrasound sensors disposed along the sensing member; an
   a support member having a first end pivotably coupled to the sensing member and a second end pivotably coupled to the support shaft;
   wherein the sensing member is configured to shift from a first configuration in which the sensing member is adjacent to the support shaft to a second configuration in which at least a portion of the sensing member extends away from the support shaft, wherein the sensing member is the only single sensing member of the medical device.

2. The medical device of claim 1, wherein the sensing member forms an arcuate shape in the second configuration.

3. The medical device of claim 2, wherein rotation of the support shaft rotates the sensing member around a longitudinal axis of the support shaft.

4. The medical device of claim 1, wherein each of the one or more ultrasound sensors are spaced away from one another along the sensing member.

5. The medical device of claim 1, wherein the distal end of the sensing member is fixedly attached to the distal end region of the support shaft.

6. The medical device of claim 1, wherein the second end of the support member is fixedly attached to the support shaft.

7. The medical device of claim 1, wherein the second end of the support member is translatable relative to the support shaft.

8. The medical device of claim 1, wherein the second end of the support member is coupled to the support shaft via an attachment collar, and wherein the attachment collar is designed to slide along the support shaft.

9. The medical device of claim 1, wherein the proximal end region of the sensing member is coupled to a hub, and wherein manipulation of the hub shifts the sensing member from the first configuration to the second configuration.

10. The medical device of claim 9, wherein rotation of a portion of the hub rotates the sensing member around a longitudinal axis of the support shaft.

11. A medical device comprising
    a support shaft having a proximal end region and a distal end region;

a sensing member having a proximal end region and a distal end region, the distal end region of the sensing member coupled to the distal end region of the support shaft;
one or more ultrasound sensors disposed along the sensing member; and
a support member having a first end coupled to the sensing member and a second end coupled to the support shaft; a hub member coupled to the proximal end region of the support shaft, the hub member including an actuator configured to move axially relative to the hub member, the actuator coupled to the proximal end of the sensing member, wherein the sensing member is configured to shift from a first configuration in which the sensing member is adjacent to the support shaft to a second configuration in which at least a portion of the sensing member moves away from the support shaft, wherein axial movement of the actuator moves the sensing member between the first configuration and the second configuration, wherein the sensing member is the only single sensing member of the medical device.

12. The medical device of claim 11, wherein rotation of a portion of the hub member is designed to rotate the ultrasound assembly around a longitudinal axis of the support shaft.

13. The medical device of claim 12, wherein rotation of a portion of the hub member is designed to sweep the sensing member along an inner surface of the bladder when the sensing member is in the second configuration.

14. The medical device of claim 11, wherein the sensing member forms an arcuate shape in the second configuration.

15. The medical device of claim 11, wherein each of the one or more ultrasound sensors are spaced away from one another along the sensing member.

16. The medical device of claim 11, wherein the distal end of the sensing member is fixedly attached to the distal end region of the support shaft.

17. The medical device of claim 11, wherein the second end of the support member is fixedly attached to the support shaft.

18. The medical device of claim 11, wherein the second end of the support member is translatable relative to the support shaft.

19. A medical device, comprising:
a support shaft having a proximal end region and a distal end region;
a sensing member having a proximal end region and a distal end region, the distal end region of the sensing member coupled to the distal end region of the support shaft;
one or more ultrasound sensors disposed along the sensing member;
a single support member having a first end pivotably coupled to the single sensing member and a second end pivotably coupled to the support shaft; and
a hub member coupled to the proximal end region of the support shaft, the hub member including an actuator configured to move axially relative to the hub member, the actuator coupled to the proximal end of the sensing member;
wherein the sensing member is configured to shift from a first configuration in which the sensing member is adjacent to the support shaft to a second configuration in which at least a portion of the sensing member extends away from the support shaft, wherein axial movement of the actuator relative to the hub member moves the sensing member between the first configuration and the second configuration, wherein the sensing member is the only single sensing member of the medical device.

* * * * *